(12) United States Patent
Miller et al.

(10) Patent No.: US 8,235,998 B2
(45) Date of Patent: Aug. 7, 2012

(54) INSTRUMENTS AND METHODS FOR IN SITU BENDING OF AN ELONGATE SPINAL IMPLANT

(75) Inventors: Keith E Miller, Germantown, TN (US); Charles A Dickinson, Bartlett, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 332 days.

(21) Appl. No.: 12/542,382

(22) Filed: Aug. 17, 2009

(65) Prior Publication Data

US 2011/0040340 A1 Feb. 17, 2011

(51) Int. Cl.
*A61B 17/70* (2006.01)
(52) U.S. Cl. .......... 606/86 A; 72/31.04; 72/297; 72/306; 29/271
(58) Field of Classification Search ................ 606/86 A, 606/99, 101, 104; 72/31.04, 296–310; 29/434, 29/260, 259, 271, 278; 269/3, 6
See application file for complete search history.

(56) References Cited

U.S. PATENT DOCUMENTS

| | | | | |
|---|---|---|---|---|
| 2,455,138 A | * | 11/1948 | Perkins | 72/158 |
| 2,693,798 A | | 11/1954 | Haboush | |
| 2,737,835 A | | 3/1956 | Herz | |
| 2,864,272 A | * | 12/1958 | Swanson | 72/310 |
| 2,873,635 A | * | 2/1959 | Waldron | 72/216 |
| 2,896,689 A | * | 7/1959 | Arms | 72/31.04 |
| 3,447,353 A | * | 6/1969 | Noveske | 72/217 |
| 4,389,872 A | * | 6/1983 | Kowal | 72/388 |
| 4,474,046 A | | 10/1984 | Cook | |
| 4,566,305 A | * | 1/1986 | Wool | 72/321 |
| 5,113,685 A | | 5/1992 | Asher et al. | |
| 5,548,985 A | | 8/1996 | Yapp | |
| 6,035,691 A | | 3/2000 | Lin et al. | |
| 6,644,087 B1 | | 11/2003 | Ralph et al. | |
| 6,673,079 B1 | * | 1/2004 | Kane | 606/105 |
| 7,454,939 B2 | | 11/2008 | Garner et al. | |
| 7,771,433 B2 | * | 8/2010 | Orbay et al. | 606/101 |
| 2005/0262911 A1 | | 12/2005 | Dankowicz et al. | |
| 2006/0150698 A1 | | 7/2006 | Garner et al. | |
| 2006/0150699 A1 | | 7/2006 | Garner et al. | |
| 2006/0235427 A1 | | 10/2006 | Thomas et al. | |
| 2006/0264973 A1 | | 11/2006 | Abdelgany | |
| 2007/0213722 A1 | * | 9/2007 | Jones et al. | 606/61 |
| 2007/0227216 A1 | | 10/2007 | Schalliol | |
| 2008/0243194 A1 | * | 10/2008 | Lotz et al. | 606/86 A |

* cited by examiner

*Primary Examiner* — Alvin Stewart
*Assistant Examiner* — Stuart S Bray

(57) ABSTRACT

Systems, instruments and methods are provided for bending an elongate spinal implant used in a medical procedure. In one form, an instrument for bending an elongate spinal implant includes a proximal handle portion and a bending mechanism having an implant engaging member movably coupled to the proximal handle portion. The bending mechanism is operable to articulate the implant engaging member relative to the proximal handle portion while a second implant engaging member associated with the articulating implant engaging member holding the elongate spinal implant in position. In another form, systems and methods are provided to bend in situ an elongate spinal implant associated with an orthopedic construct.

14 Claims, 9 Drawing Sheets

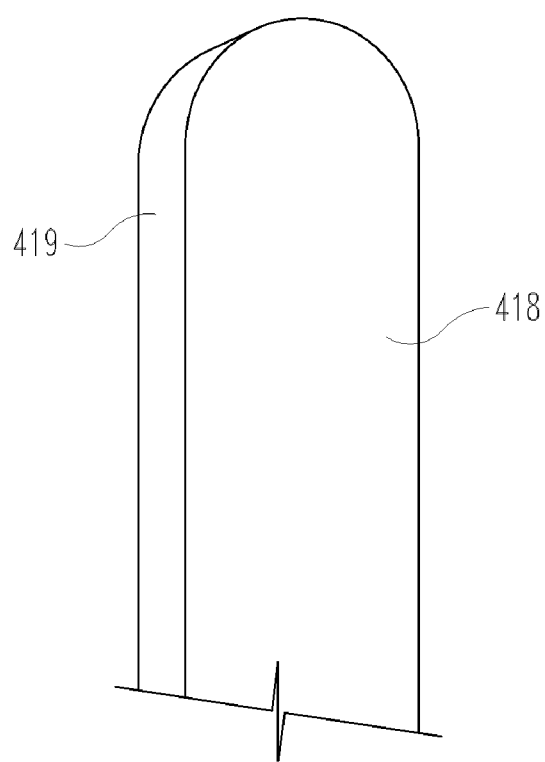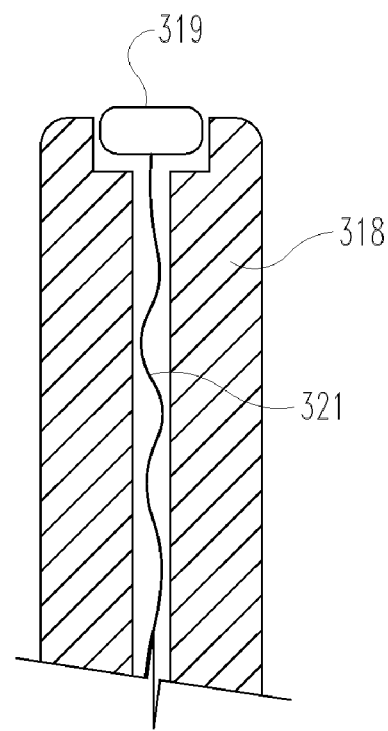
*Fig. 14*  *Fig. 15*

INSTRUMENTS AND METHODS FOR IN SITU BENDING OF AN ELONGATE SPINAL IMPLANT

BACKGROUND

The present invention generally relates to systems, instruments and methods for bending an elongate spinal implant used in association with a medical procedure. In one form, the medical procedure is a spinal stabilization procedure wherein an orthopedic construct is engaged along the spinal column, and the elongate spinal implant is a rod component anchored to the spinal column by a number of bone anchors.

The use of spinal constructs to stabilize and support a portion of the spinal column has become commonplace. In particular, spinal constructs frequently include several bone anchors that are anchored to various portions of the spinal column, and an elongate rod that extends between and is engaged with the bone anchors to provide stabilization and support to the spinal column. Typically, the elongate rod is initially provided in a substantially straight configuration, and is subsequently bent or contoured to facilitate engagement with each of the bone anchors and/or to provide a desired spinal curvature.

In the past, bending or contouring of elongated rods in situ was accomplished by instruments or tools that relied solely on manual application of a mechanical bending force. However, prior techniques and instrumentation involve applying bending forces to the spinal rod prior to implantation, resulting in a less than optimal fit between the bone anchors, or requiring multiple attempts to bend and implant the spinal rod to achieve the desired fit. Other techniques and instrumentation for bending of spinal rods required manual application of excessive bending forces, and also risked fracturing or weakening of the elongate rod and/or degrading the material properties associated with the elongate rod. Furthermore, bending of spinal rods in situ, i.e. when implanted in the patient, present difficulties due the small space available to maneuver the surgical instruments, and the risk of inadvertent damage to tissue should the instrument be mishandled or too much force applied to bend the spinal rod. In this arena, the desire persists for improved implant bending/contouring capabilities. Thus, there is a need for additional contributions in this area of technology.

SUMMARY

One nonlimiting embodiment of the present invention is directed to an instrument for bending an elongate spinal implant used in association with a medical procedure. In one form of the present invention, the medical procedure is a spinal stabilization procedure, and the elongate implant is a spinal rod component anchored to the spinal column by a number of bone anchors. However, bending of other types of elongate implants is also contemplated by the present invention. Additionally, in one or more forms, the elongate spinal implant is formed of a heat deformable material which softens as it is heated to provide increased flexibility to facilitate bending/contouring of the elongate spinal implant.

Systems, instruments and methods are provided for in situ bending an elongate spinal implant that include an instrument for bending the elongate spinal implant. The instrument includes a proximal handle portion and a bending mechanism having an implant engaging member movably coupled to the proximal handle portion. The bending mechanism is operable to articulate the implant engaging member relative to the proximal handle portion without requiring the proximal handle portion to be maneuvered.

One embodiment of the present application includes an instrument for bending an elongate surgical implant that includes at least one proximal handle portion extending along a longitudinal axis between a proximal end and a distal shaft portion opposite the proximal end. The instrument includes a bending mechanism with first and second implant engaging members, where at least one of the implant engaging members is pivotally coupled to the distal shaft portion. The bending mechanism further includes a first drive member coupled to the distal shaft portion and a second drive member coupled to the implant engaging member. The instrument is operable to articulate the pivotally coupled implant engaging member relative to the distal shaft portion and to the other implant engaging member to change an angular orientation of the implant engaging member relative to the longitudinal axis to apply a bending force to the elongate surgical implant.

Another embodiment includes a system comprising a first bending instrument and a second bending instrument laterally spaced from the first bending instrument. Each of the first and second bending instruments includes an elongate handle portion extending along a longitudinal axis and a distal shaft portion extending distally from the elongate handle portion along the longitudinal axis and an implant engaging member that defines a channel, the implant engaging member extending distally from the distal shaft portion. At least one of the first and second bending instruments includes a bending mechanism that includes the implant engaging member pivotally coupled to the distal shaft portion thereof, a first drive member coupled to the distal shaft portion, and a second drive member coupled to the implant engaging member and connected with the first drive member. At least one of the first and second drive members is movable to rotate the implant engaging member about the pivotal coupling location to change an angle of orientation of the implant engaging member relative to the longitudinal axis. The system also includes an elongate spinal implant extending through the channels of the implant engaging members when the implant engaging members are in a first angular orientation relative to the longitudinal axis. Rotation of the at least one of the first and second drive members of the at least one of said first and second bending instruments moves the implant engaging member from the first angular orientation to a second angular orientation while the other of the first and second bending instruments maintains the elongate spinal implant in position, and the spinal implant is bent as the implant engaging member moves from the first angular orientation to the second angular orientation.

Another embodiment of the present application includes a method for bending an elongate spinal implant associated with an orthopedic construct within a patient. The method comprises providing an elongate spinal implant; providing an instrument including a proximal handle portion and a bending mechanism structured to receive a portion of the elongate spinal implant, the instrument further including an actuation system connected to the handle portion and the bending mechanism; positioning a portion of the elongate spinal implant within first and second engaging members of the bending mechanism when the elongate spinal implant is in the patient; and bending the elongate spinal implant by actuating the bending mechanism to articulate at least one of the first and second implant engaging members relative to the other of the first and second implant engaging members while holding the elongate spinal implant in position with the other of the first and second implant engaging members.

Another embodiment of the present application is directed to a unique system and method for in situ bending an elongate spinal implant used in association with a spinal implant construct. Other embodiments include unique methods, systems, devices, kits, assemblies, equipment, and/or apparatuses directed to the bending or contouring of an elongate spinal implants.

Further embodiments, forms, features, aspects, benefits, objects and advantages of the present invention shall become apparent from the detailed description and figures provided herewith.

BRIEF DESCRIPTION OF THE FIGURES

FIG. 14 is an elevation view of another embodiment handle of the bending instrument.

FIG. 15 is a longitudinal section view of another embodiment handle of the bending instrument.

DESCRIPTION OF THE ILLUSTRATED EMBODIMENTS

Figure 1:
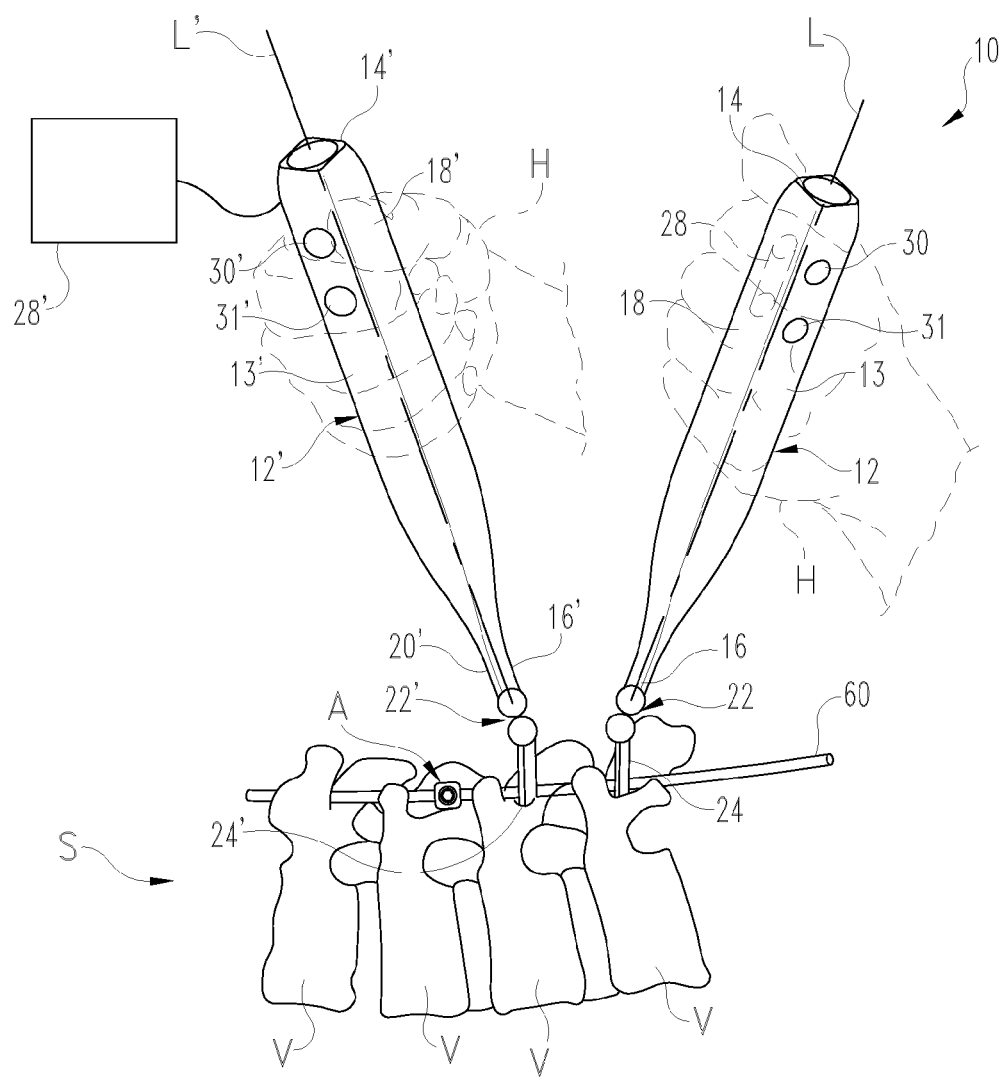
FIG. 1 is an elevational perspective view of one embodiment system for in situ bending of an elongate spinal implant.

For the purposes of promoting an understanding of the principles of the invention, reference will now be made to the embodiments illustrated in the drawings and specific language will be used to describe the same. It will nevertheless be understood that no limitation on the scope of the invention is intended. Any alterations and further modifications in the illustrated devices and described methods and further applications of the principles of the invention as disclosed herein are contemplated as would normally occur to one skilled in the art to which the invention relates.

Systems, instruments and methods for bending or contouring an elongate spinal implant used in association with a spinal medical procedure are provided. In one form, the medical procedure is a spinal stabilization procedure wherein a spinal construct is engaged along the spinal column to two or more vertebrae. In a further form, the elongate implant is a rod component anchored to the spinal column by a number of bone anchors to provide stabilization and support to the spinal column. However, other types of elongate implants are also contemplated for use in association with the present invention, including plate components or other suitable types of elongate support components. In one embodiment, the bone anchors are initially anchored to portions of the spinal column, followed by engagement of the elongate implant to the bone anchors. The elongate implant may require bending or contouring in situ to allow for interconnection with the bone anchors and/or to provide a desired spinal curvature. The spinal construct may be used in association with, but is not limited to, treatment of degenerative spondylolisthesis, fracture, dislocation, scoliosis, kyphosis, or spinal tumors.

Referring to FIG. 1, illustrated therein is a system 10 that includes a pair of laterally spaced bending instruments 12, 12' for bending or contouring an elongate rod 60. However, as indicated above, other types of elongate members are also contemplated for use in association with the present invention, including plate components or other suitable types of elongate support components. The instruments 12, 12' extend along a longitudinal axis L, L' and generally include first elongated handle members 13, 13', respectively, engageable by hand H of a user, such as a surgeon. Each of the elongated handle members 13, 13' extends between a proximal end 14, 14' and a distal end 16, 16', and includes a manual gripping portion 18, 18' adjacent the proximal end 14, 14' and a distal shaft portion 20, 20' extending distally from manual gripping portion 18, 18' to distal end 16, 16'. The gripping portions 18, 18' can be provided with knurling, outer silicone or rubber grip, ergonomic handgrips, or other structure to facilitate gripping by a surgeon or other medical personnel. In still other embodiments, the gripping portions 18, 18' need not be provided with any special gripping features.

The instruments 12, 12' also each include a bending mechanism 22, 22' structured to bend or contour the elongate rod 60 at one or more axial locations along the length of the rod 60. In the illustrated embodiment, the bending mechanisms 22, 22' further each include an implant engaging member 24, 24' that have a generally open configuration and are structured and arranged to facilitate placement around rod 60 when rod 60 is positioned in situ. As used herein, in situ means the rod 60 or other elongate spinal implant is in the patient and engaged to one or more vertebra V of spinal column S. In the illustrated embodiment, rod 60 is engaged to the pedicles of one or more vertebrae V with a bone anchor A. Instruments 12, 12' are laterally spaced from one another along rod 60 and are movable along the axial length of rod 60 to adjust the lateral spacing therebetween to direct instruments 12, 12' to locations where bending of rod 60 is desired. Thus, rod 60 provides a mechanical link between the engaging members 24, 24' of instruments 12, 12' while hands H hold handles portions 13, 13'. In other embodiments discussed below, a separate linking member that is not part of the implanted construct is provided to couple instruments 12, 12' to one another in addition to spinal rod 60.

Bending mechanisms 22, 22' are each operable by an actuating system including a controller and a motor associated with respective handle portion 13, 13' that are connected with the respective bending mechanism 22, 22'. The controller and motor are operable to pivot or articulate the respective implant engaging member 24, 24' to change an angular orientation of the respective implant engaging member 24, 24' relative to longitudinal axis L, L' of the corresponding handle portion 13, 13' when spinal rod 60 is engaged to the implant engaging members 24, 24'. When one of the rod engaging members 24, 24 is articulated, the other rod engaging member 24, 24' is held in position by the user so that articulation of the one rod engaging member 24' 24' applies a bending force to the spinal rod 60 without maneuvering the handle portion 13, 13' from which the rod engaging member 13, 13' extends. As used herein, maneuvering the proximal handle portion 13, 13' means that the handle portion 13, 13' is moved or manipulated with sufficient force to bend spinal rod 60 with its implant engaging portion 24, 24'. It should be understood that bending forces can be applied to rod 60 by simultaneously or alternately articulating the rod engaging member 24, 24' of each of the bending mechanisms 22, 22'. It should also be understood that the system may be provided with only one of the bending instruments including an articulating rod engaging member, while the rod engaging member of the other bending instrument is fixed relative to its handle portion.

As illustrated in FIG. 1, the implant engaging members 24, 24' are angled relative to the respective longitudinal axis L, L' to form an angular orientation with longitudinal axis L, L'. Implant engaging members 24, 24' are each movable with the respective bending mechanism 22, 22' to pivot about distal shaft portion 20, 20' to change its angular orientation from an aligned orientation where implant engaging members 24, 24' are aligned and co-linear with the respective longitudinal axis L, L' to angular arrangements ranging from +90 degrees to −90 degrees from the aligned orientation. Bending mechanism 22, 22' are coupled to an actuating system that includes a motor, as discussed further below, to provide power to actuate bending mechanisms 22, 22' and change the angular orientation of implant engaging members 24, 24'. In one embodiment shown with respect to instrument 12, an internal power source 28 in grip portion 18 provides power to the motor to actuate bending mechanism 22 to articulate implant engaging member 24. In another embodiment shown with respect to instrument 12', an external power source 28' is tethered to instrument 12' to provide power to the motor to actuate bending mechanism 22' and articulate implant engaging member 24'. Of course it should be understood that either or both of instruments 12, 12' may employ an internal power source or an external power source within the same system.

Furthermore, grip portions 18, 18' can include user inputs 30, 31 and 30', 31' to allow the user to selectively start and stop articulation of bending mechanisms 22, 22', and also to control the direction of articulation of bending mechanisms 22, 22' relative to longitudinal axes 12, 12'. User inputs 30, 31 and 30', 31' may be in the form of a keypad with push buttons, knobs, touch screen, or other suitable input system to provide user commands to the actuating system.

Figure 2:
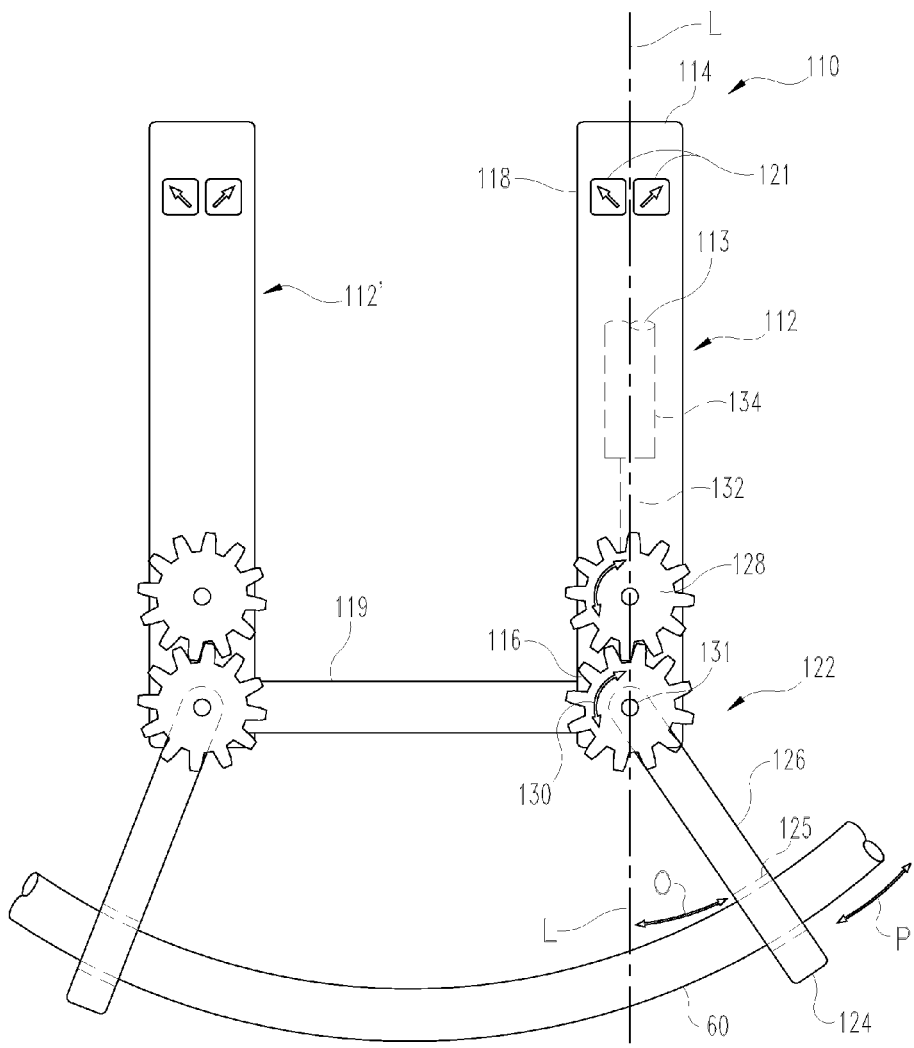
FIG. 2 is a side view of another embodiment system with laterally spaced bending instruments coupled to the elongate spinal implant.

Referring now to FIG. 2, there is shown another embodiment system 110 that is similar to system 10 discussed above, and includes a first instrument portion 112 and a second bending instrument portion 112' connected to one another with a rigid coupling arm 119 extending laterally from the distal shaft portions of the instrument portions 112, 112'. Bending instrument portions 112 and 112' are substantially identical to one another, so only instrument portion 112 will be described in further detail. Furthermore, bending instrument portions 112, 112' may include any of the features of bending instruments 12, 12' and the other bending instruments and instrument portions discussed herein. Bending instrument portion 112 extends along longitudinal axis L and generally includes a first elongated handle member 113 extending between a proximal end 114 and a distal end 116. Handle member 113 includes a manual gripping portion 118 adjacent the proximal end 114 and a distal shaft portion 120 extending distally from manual gripping portion 118 to distal end 116.

The instrument portion 112 also includes a bending mechanism 122 coupled to distal shaft portion 120. Bending mechanism 122 includes an implant engaging member 124 with a channel 125 adjacent a distal end thereof that receives rod 60 therein even when rod 60 is implanted in the patient. Implant engaging member 124 also includes a coupling portion 126 extending proximally from channel 125 to distal shaft portion 120 where coupling portion 126 is rotatably mounted to distal shaft portion 120. The portion of implant engaging member 124 with channel 125 can be separate from or formed as one piece with coupling portion 126. In one embodiment, implant engaging member 124 includes a C-shaped channel extending into one side of a bar that extends from coupling portion 126, and the channel 125 is sized to fit laterally over a side of rod 60. Other embodiments contemplate implant engaging members 124 that completely encircle rod 60, or that include two or more parts that clampingly engage rod 60 or that capture rod 60 in engagement with the bending instrument.

Bending mechanism 122 also includes a first drive member 128 rotatably coupled to distal shaft portion 120 and implant engaging member 124 includes a second drive member 130 fixedly coupled thereto about rotation axis 131. Second drive member 130 is connected with first drive member 128. An actuator 132 in handle portion 113 is coupled to first drive member 128, and actuator 132 is coupled to motor 134. Controls 121 receive input that operates motor 134, which is operable to move actuator 132 which in turn rotates first drive member 128 in a selected direction about its rotatable coupling with distal shaft portion 120. Rotation of first drive member 128 angularly displaces second drive member 130 about axis 131, and thus displaces implant engaging member 124, along an arc that is concentric with the rotational path of first drive member 128. Implant engaging member 124 thus follows an arced pivot path P to change the angular orientation O of implant engaging member 124 relative to longitudinal axis L from a 0 (zero) degree orientation that is aligned with longitudinal axis L to angular orientations O ranging from at least −90 degrees to at least +90 degrees from longitudinal axis L.

Figure 3:
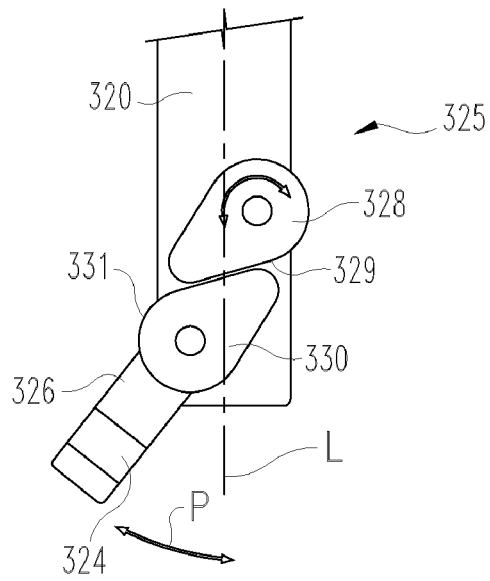
FIG. 3 is an elevational view of another embodiment bending mechanism of the bending instrument.

In the illustrated embodiment of FIG. 2, first and second drive members 128, 130 are gear-type members with outer peripheral teeth that mesh with one another so that rotation of first drive member 128 about its center drives second drive member 130 so that it drives implant engaging member 124 along path P around axis 131. Other embodiments contemplate other configurations for the bending mechanism. For example, FIG. 3 shows a distal portion of a bending instrument or instrument portion where the proximal portions of the instrument not shown can be configured identically to the other bending instrument embodiments described herein. The bending instrument of FIG. 3 includes a bending mechanism 322 that includes a first drive member 328 in the form of a first cam and a second drive member 330 in the form of a second cam. First drive member 328 and coupling portion 326 of implant engaging portion 324 are rotatably coupled to distal shaft portion 320 of the bending instrument, and second drive member 330 is fixedly coupled to coupling portion 326 so that rotation of first drive member 328 changes the location in which eccentric cam surface 329 contacts the eccentric cam surface 331 of second drive member 330, resulting in articulation of implant engaging member 324 along pivot path P to change the angular orientation of implant engaging member 324 relative to longitudinal axis L.

Figure 4:
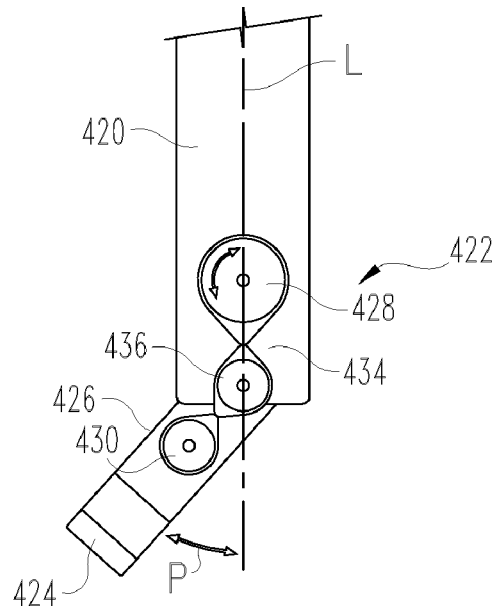
FIG. 4 is an elevational view of another embodiment bending mechanism of the bending instrument.

In another example, FIG. 4 shows a distal portion of another embodiment bending instrument or instrument portion where the proximal portion of the instrument not shown can be configured identically to the other bending instrument embodiments described herein. The bending instrument of FIG. 4 includes a bending mechanism 422 that includes a first drive member 428 in the form of a first pulley and a second drive member 430 in the form of a second pulley. First drive member 428 and coupling portion 426 are rotatably coupled to distal shaft portion 420 of the bending instrument, and second drive member 430 is fixedly coupled to coupling arm 326 so that rotation of first drive member 328 in one direction reduces the length of drive belt 434 around roller 436 and pulls driver member 426 in the desired direction, resulting in articulation of implant engaging member 424 along pivot path P to change the angular orientation of implant engaging member 424 relative to longitudinal axis L.

Figure 5:
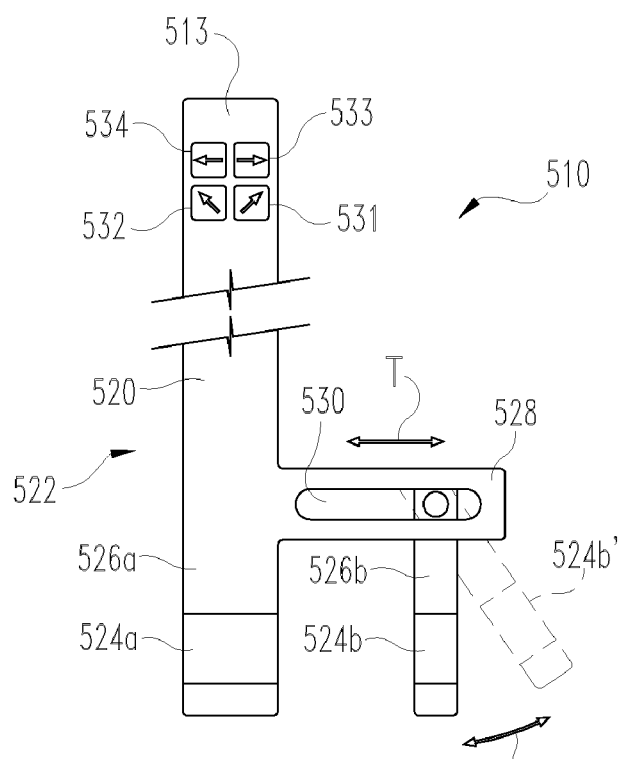
FIG. 5 is an elevational view of another embodiment bending instrument.

In another example, FIG. 5 shows a distal portion of a bending instrument 510, and the proximal portion 513 of the bending instrument 510 can be configured identically to the other bending instruments described herein. The distal portion in FIG. 5 includes another embodiment bending mechanism 522 that includes a first implant engaging member 524a with a first coupling portion 526a extending distally from and fixed relative to distal shaft portion 520 on longitudinal axis L. A second implant engaging member 524b is offset laterally from first implant engaging member 524a. Second implant engaging member 524b includes a coupling portion 526b that is pivotally mounted to a rigid arm 528 that extends laterally from distal shaft portion 520. Laterally extending arm 528 includes an elongated slot or channel 530 along which second coupling portion 526b can be moved to adjust the lateral spacing along translation path T between implant engaging members 524a and 524b. Furthermore, second implant engaging member 524b can be rotated about laterally extending arm 528, resulting in articulation of second implant engaging member 524b along pivot path P to change the angular orientation of second implant engaging member 524b relative to longitudinal axis L and relative to first implant engaging member 524a.

In one embodiment, instrument 510 includes a first set of controls 533, 534 operable to receive input and provide signals to the actuator to adjust the lateral spacing between implant engaging members 524a, 524b by moving implant engaging member 524b along slot 530 along translation path T. Instrument 510 further includes a second set of controls 531, 532 operable to receive input and provide signals to the actuator to adjust the angular orientation of implant engaging member 524b by pivoting implant engaging member 524b along path P relative to the implant engaging member 524a. The elongate spinal implant engaged to implant engaging members 524a, 524b is thus bent with implant engaging member 524a holding the elongate implant in position while implant engaging member 524b articulates to bend the elongate spinal implant.

Figure 6:
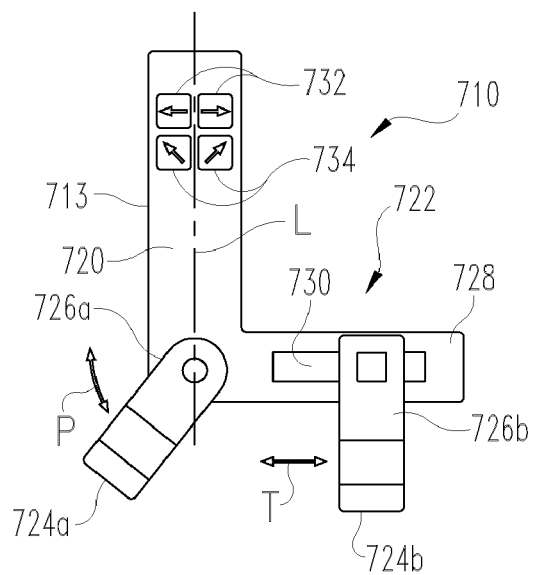
FIG. 6 is an elevational view of another embodiment bending instrument.

In another variation of the FIG. 5 embodiment, FIG. 6 shows a distal portion of a bending instrument 710, and the proximal portion 713 of the bending instrument 710 can be configured identically to the other bending instruments described herein. The distal portion in FIG. 6 includes another embodiment bending mechanism 722 that includes a first implant engaging member 724a with a first coupling portion 726a extending distally from and pivotally coupled to distal shaft portion 720 on longitudinal axis L. A second implant engaging member 724b is offset laterally from first implant engaging member 724a. Second implant engaging member 724b includes a coupling portion 726b that is non-pivotally mounted to a rigid arm 728 that extends laterally from distal shaft portion 720. Laterally extending arm 728 includes an elongated slot or channel 730 along which second coupling portion 726b can be moved along translation path T to adjust the lateral spacing between implant engaging members 724a and 724b. Furthermore, first implant engaging member 724a can be rotated about distal shaft portion 720, resulting in articulation of first implant engaging member 724a along pivot path P to change the angular orientation of first implant engaging member 724a relative to longitudinal axis L and relative to second implant engaging member 724b.

Instrument 710 includes a first set of controls 732 operable to receive input and provide signals to the actuator to adjust the lateral spacing between implant engaging members 724a, 724b by moving implant engaging member 724b along slot 730 along translation path T. Instrument 710 further includes a second set of controls 734 operable to receive input and provide signals to the actuator to adjust the angular orientation of implant engaging member 724a by pivoting implant engaging member 724a along path P relative to the implant engaging member 724b. The elongate spinal implant engaged to implant engaging members 724a, 724b is thus bent with implant engaging member 724b holding the elongate implant in position while implant engaging member 724a articulates to bend the elongate spinal implant.

Figure 7:
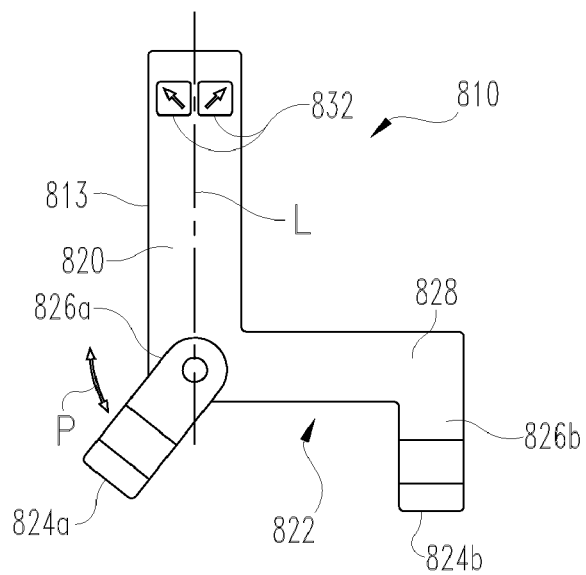
FIG. 7 is an elevational view of another embodiment bending instrument.

In another variation of the FIG. 5 embodiment, FIG. 7 shows a distal portion of a bending instrument 810, and the proximal portion 813 of the bending instrument 810 can be configured identically to the other bending instruments described herein. The distal portion in FIG. 7 includes another embodiment bending mechanism 822 that includes a first implant engaging member 824a with a first coupling portion 826a extending distally from and pivotally coupled to distal shaft portion 720 on longitudinal axis L. A second implant engaging member 824b is offset laterally from first implant engaging member 824a. Second implant engaging member 824b includes a coupling portion 826b that is fixed to a rigid arm 828 that extends laterally from distal shaft portion 820. First implant engaging member 824a can be rotated about distal shaft portion 820, resulting in articulation of first implant engaging member 824a along pivot path P to change the angular orientation of first implant engaging member 824a relative to longitudinal axis L and relative to second implant engaging member 824b. Instrument 810 includes a set of controls 832 operable to receive input and provide signals to the actuator to the actuator to adjust the angular orientation of implant engaging member 824a by pivoting implant engaging member 824a along path P relative to the implant engaging member 824b. The elongate spinal implant engaged to implant engaging members 824a, 824b is thus bent with implant engaging member 824b holding the elongate implant in position while implant engaging member 824a articulates to bend the elongate spinal implant.

Figure 8:
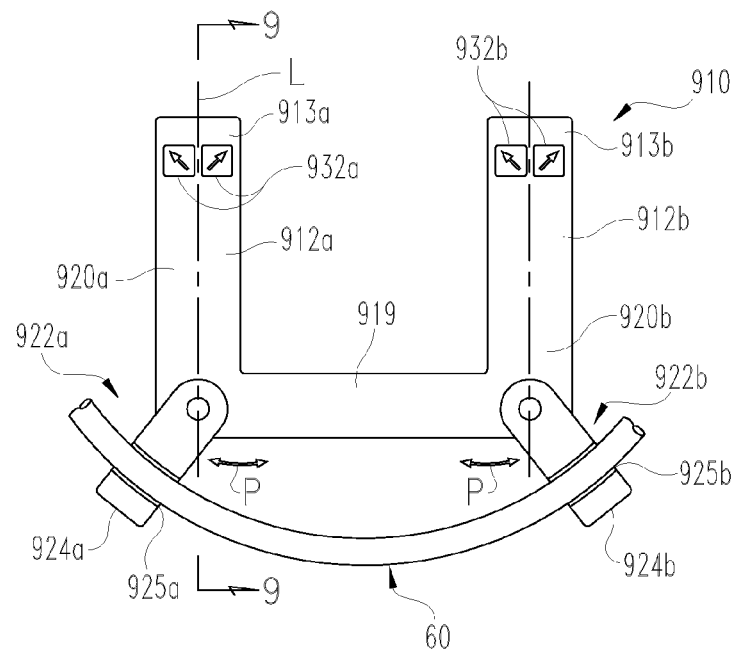
FIG. 8 is an elevational view of another embodiment bending instrument mounted to an elongate spinal implant.
Figure 9:
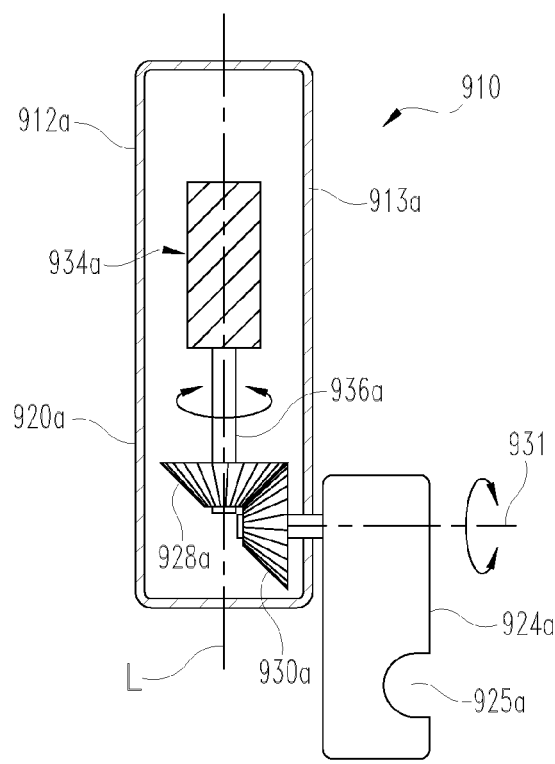
FIG. 9 is a section view along line 9-9 of FIG. 8.

FIGS. 8-9 show another embodiment bending instrument 910 that is similar to bending instrument 110 of FIG. 2, and like components will not be discussed. Bending instrument portions 912a, 912b are laterally spaced from one another and rigidly coupled to one another with an arm 919 extending therebetween adjacent the distal ends of portions 912a, 912b. Bending instrument portions 912a, 912b each extend along longitudinal axis L, L', respectively, and generally include elongated handle member 913a, 913b with bending mechanism controls 932a, 932b and a distal shaft portion 920a, 920b. The instrument portions 912a, 912b also each include a bending mechanism 922a, 922b coupled to distal shaft portion 920a, 920b and controls 932a, 932b, respectively. Bending mechanisms 922a, 922b each include an implant engaging member 924a, 924b with a channel 925a, 925b adjacent a distal end thereof that receives rod 60 therein even when rod 60 is implanted in the patient.

As shown in FIG. 9, a section of instrument portion 912a is provided, it being understood that a section view of second instrument portion 912b can be substantially identical to the section of instrument portion 912a. Bending mechanism 922a includes a first drive member 928a rotatably mounted within distal shaft portion 920a and implant engaging member 924a includes a second drive member 930 fixedly coupled thereto about rotation axis 931. Second drive member 930 is connected with first drive member 928 with a bevel gear type arrangement. An actuator 936a in handle portion 913a is coupled to first drive member 928a, and actuator 932a is coupled to motor 934a. Controls 932a receive input that operates motor 934a, which is operable to move actuator 932b which in turn rotates first drive member 928a in a selected direction about longitudinal axis L. Rotation of first drive member 928a rotates second drive member 930a, which angularly displaces implant engaging member 924a along an arced pivot path P to change the angular orientation of implant engaging member 924a relative to longitudinal axis L.

Figure 10:
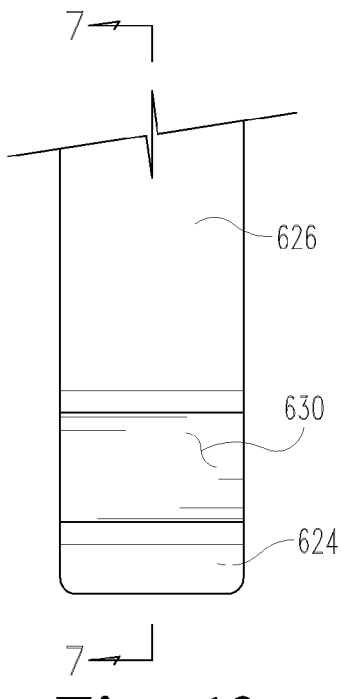
FIG. 10 is an elevation view of another embodiment implant engaging member of the bending instrument.
Figure 11:
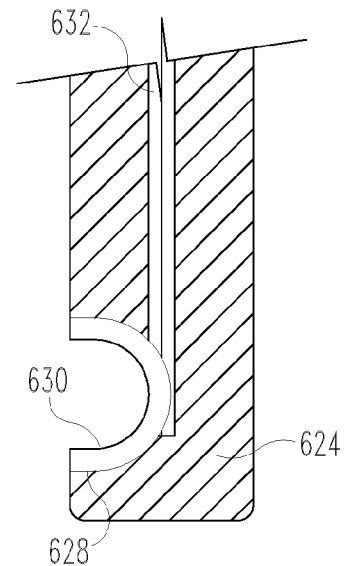
FIG. 11 is a section view along line 11-11 of FIG. 10.

Various configurations for the implant engaging members of the bending instruments discussed herein are also contemplated. For example, FIGS. 10-11 show an implant engaging member 624 that includes a C-shaped channel 628 in a coupling portion 626 that extends from the proximal portion of the bending instrument. Implant engaging member 624 and coupling portion 626 can be employed with any of the bending mechanism and bending instrument embodiments discussed herein. A heating element 630 resides in channel 628 so that the heating element 630 contacts the outer surface of the portion of rod 60 is positioned in channel 628. A wire 632 extends from heating element 630 through coupling portion 626 and to the proximal portion of the instrument, where it can be coupled to a controller and/or heater that provides energy necessary to change the temperature of heating element 630 to heat rod 60.

In the embodiment of the instrument illustrated in FIGS. 10-11, the heating element 630 is generally positioned over a select portion or length of the rod 60. In this arrangement, the heating element 630 provides a relatively uniform application of heat to the rod portion against which it is positioned. Configurations of the heating element 630 other than the configuration illustrated in FIGS. 10 and 11 are also contemplated. For example, the heating element 630 can be configured to completely encircle rod 60, or be clamped to rod 60. It is also contemplated that the bending instrument need not necessarily include a heating element in channel 628, with the heating element alternatively being coupled directly to one of the distal shaft portion, bending mechanism or other portion of the bending instrument.

The heating element 630 is generally structured to heat a length of the rod 60 positioned in channel 628. The heating element 630 may take any form or configuration suitable to provide heat to the selected portion of the rod 60. For example, the heating element 630 may be configured to provide heat via convection heating, conduction heating, infrared heating, or any other type of heating known to those of skill in the art. Additionally, the heating element 630 may utilize power from an internal or external power source to provide heat in a variety of manners including, for example, via a coil resistance heater, a metal oxide resistance heater, or a PTC (Positive Temperature Coefficient) heater, just to name a few possibilities.

The heat applied to the selected portion of the rod 60 by the heating element 630 facilitates bending of the rod 60 to a desired configuration having a particular curvature or contour. In one embodiment of the invention, the rod 60 is formed from one or more heat deformable materials. In a more specific embodiment, the heat deformable material(s) comprises one or more thermoplastic polymers. Examples of thermoplastic polymers include, for example, high molecular weight organic polymers. More particular examples of thermoplastic polymers include, without limitation, polycarbonate, polyketone, polyester, polyethylene, polyetheretherketone (PEEK), polyimide, polylactic acid, polypropylene, polystyrene, polysulfone, polyvinyl chloride, polyamide, poly(tetrafluoroethene), polyphthalamide, polybutylene and mixtures thereof, just to name a few possibilities. In one particular embodiment, the rod 60 is formed from a polyetheretherketone (PEEK) material. It is also contemplated that the rod 60 may be formed of other materials which, when heated, facilitate bending of the rod 60 to a desired configuration having a particular curvature or contour. For example, the rod 60 may be formed from one or metals or metal alloys which are amenable to increased flexibility when heated.

Figure 12:
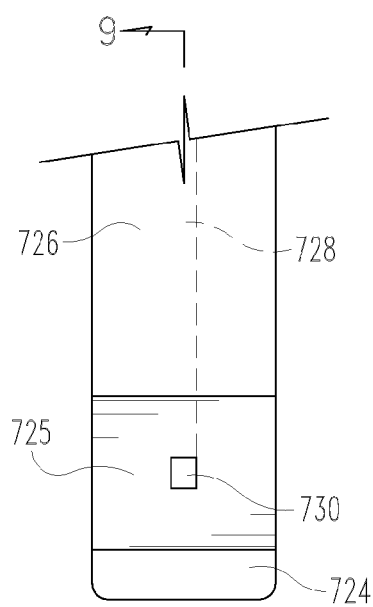
FIG. 12 is an elevation view of another embodiment implant engaging member of the bending instrument.
Figure 13:
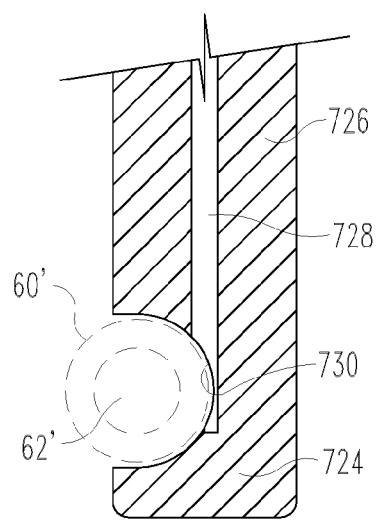
FIG. 13 is a section view along line 13-13 of FIG. 12.

Referring to FIGS. 12 and 13, there is shown another embodiment for the implant engaging members, which can be employed with any of the bending instrument embodiments discussed herein. Implant engaging member 724 includes a channel 725 and a coupling portion 726 extending to a distal shaft portion of the bending instrument. Coupling portion 726 includes an axial lumen or passage 728 extending proximally and distally therethrough. Passage 728 can open along a side of coupling portion 726 proximally of channel 725, or extend proximally through all or a portion of the length of the distal shaft portion and/or proximal handle portion of the bending instrument. Passage 728 opens into channel 725 at a port 730, which communicates with or is otherwise coupled to a spinal rod 60'. A bone cement, resin or other desired or suitable substance can be injected through passage 728 and out of port 730, and then into a lumen 62' of rod 60', or into a recess or other portion in an external surface of rod 60', when the rod 60' is positioned in channel 725. The passage 62' or other surface configuration of rod 60' facilitates bending of rod 60' with the bending instrument, and when the desired bending configuration is obtained, the cement or resin is injected into or around the rod 60' to maintain the bent configuration achieved by the bending instrument.

Various embodiments for the grip portion 18 of handle portion 13 of bending instrument 10 are also contemplated. For example, FIG. 14 shows another embodiment grip portion 418 similar to grip portion 18 discussed above, but with a pressure sensing pad 419 along the outer surface thereof that can sense the pressure applied to grip portion 418 by the hand of the user. The sensing part 419 is connected to a controller that converts the sensed pressure or force applied to sensing part 419 and provides a signal to the motor to actuate the bending mechanism so it articulates the rod engaging member to apply a force to bend the rod that corresponds to the sensed gripping pressure.

In another example, FIG. 15 shows a grip portion 318 similar to grip portion 18 discussed above, but grip portion 318 includes a voice recognition system 319 that can recognize verbal inputs by the user to bend the rod a desired amount. Voice recognition system 319 is coupled to a controller with a lead 321 extending in grip portion 318 to a controller of the bending instrument, or extending externally to an external controller (not shown). The amount of bending can be verbally specified in units corresponding to the degree of curvature to be applied to the rod, the amount of force to be applied to the rod, or the pressure to be exerted in the rod, for example.

Figure 16:
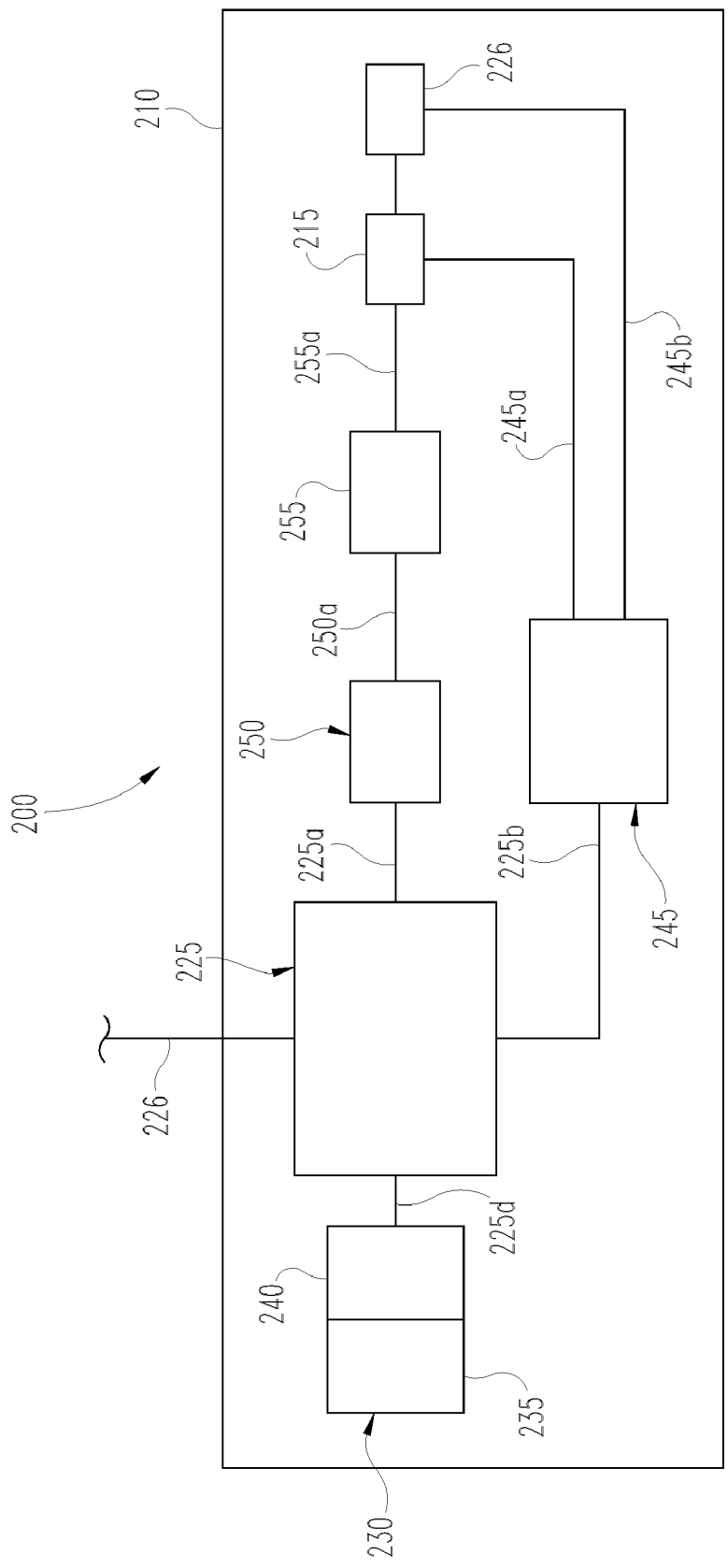
FIG. 16 is a schematic diagram illustrating one embodiment of a system of the bending instrument for bending the elongate spinal implant.

Referring now to FIG. 16, shown therein is a schematic illustration of a system 200 for bending the rod 60 to a desired curvature or contour. The system 200 includes a rod bending instrument 210 that includes a bending mechanism 215 and, in some embodiments, a heating element 220. It should be appreciated that the bending instrument 210 and bending mechanism 215 may be configured like any of the bending instrument and bending mechanism embodiments illustrated and described herein. Additionally, various features and characteristics described above with respect to the heating element 630 are equally applicable to the heating element 220. Besides the instrument 210 and bending mechanism 215, the system 200 may also be provided with a controller 225, a user input or interface 230, a sensing arrangement 245 and a motor 250. The system 200 also includes an actuating member 255 for regulating or controlling actuation of the bending mechanism 215 with motor 250.

The sensing arrangement 245 includes one or more sensors structured to monitor one or more operating functions associated with the instrument 210. For example, the operating functions monitored by the sensing arrangement 245 may include sensing and monitoring of the temperature of heat applied by the heating element 220 to the rod 60, the pressure applied to rod 60 and/or gripping pad 419, the force applied to the rod by bending mechanism 215, and/or the angular orientation of bending mechanism 215 relative to the longitudinal axis of the bending instrument. More particularly, in the illustrated embodiment, the sensing arrangement 245 is electronically coupled to the bending mechanism 215 via pathway 245a and includes a sensor configured for monitoring the amount of pressure applied on the rod 60 by the bending mechanism 215 and/or the angular orientation of bending mechanism 215 relative to a datum, such as the longitudinal axis of instrument 210. The sensing arrangement 245 is also electronically coupled with the heating element 220 via pathway 245b and includes a temperature sensor for monitoring the temperature of the heat applied by the heating element 220 to the rod 60. In one embodiment, the sensing arrangement 245 may be structured to sense the heat being applied to the rod 60 by the heating element 220, or may alternatively be structured to sense the temperature of the rod 60 itself. In another embodiment, the sensing arrangement 245 may be structured to sense the temperature of the bending mechanism 215. The sensing arrangement 245 is further structured to provide an electronic sensor signal corresponding to the sensed orientation, pressure and/or temperature to the controller 225 along pathway 225b.

The controller 225 operates in accordance with operating logic to receive and process the sensor signal to determine if a change in temperature, angular orientation and/or pressure is necessary. Particularly, it may be desired to maintain a particular balance of the temperature and pressure to avoid undesired deformation or fracturing/breaking of the rod 60. For example, excessive heat could possibly cause the rod 60 to melt and/or negatively affect the material properties of the rod 60, while excessive pressure could cause rod the 60 to improperly notch, deform or break and/or negatively affect the material properties of the rod 60. In one embodiment, the controller 225 is comprised of one or more components that may be configured as a single unit, or may alternatively be distributed among two or more units. Such components may be of a solid state, electromagnetic, optical, and/or other configurations that would occur to those skilled in the art. The controller 225 may include analog circuitry, digital circuitry, and/or a hybrid combination of both of these types. In one embodiment, the controller 225 is of the programmable variety that executes algorithms and processes data in accordance with its operating logic being defined by programming instructions (such as software or firmware). Alternatively or additionally, the operating logic for the controller 225 is at least partially defined by hardwired logic or other hardware. Controller 225 may reside within the handle portion of the bending instrument, or be located externally to the bending instrument and electrically coupled to the bending instrument during use.

As illustrated in FIG. 16, the controller 225 includes a power supply 226 which may supply power to the controller 225 from an external source, such as an electrical socket. In another embodiment, a power supply is located internally within the bending instrument 210 and may be provided, for example, in the form of one or more electrochemical cells or a battery of such cells. It should be appreciated that the controller 225 may be modified for use with a DC power source or an AC power source, and that the modification of components may be dependent upon the availability of one or more forms of the power source. Additional variations to the controller 225 will become apparent with respect to various configurations of the system 200. It should also be appreciated that the controller 225 may provide power to the other components of the system 200.

After the controller 225 receives and processes the sensor signal, a controller output signal is sent to the user interface 230 via pathway 225d. As one example, the controller output signal can include an angular orientation of the implant engaging member, a temperature output signal and/or a pressure output signal. The user interface 230 may include a display 235 configured to provide an indication corresponding to the output signal to a user, and which may identify the change, if any, needed to one or both of the temperature and pressure. The display 235 can be of a Cathode Ray Tube (CRT) type, Liquid Crystal Display (LCD) type, plasma type, Organic Light Emitting Diode (OLED) type, a printer, or other types as would occur to those skilled in the art. The user interface 230 may also include a user input 240 wherein a user may enter one or more commands in response to the indication provided by the display 235. Additionally or alternatively, a user may enter other information at the user input 240 relevant to the bending process, such as the type of material from which the rod 60 is formed, the force or pressure to be applied during bending, the desired angular movement or orientation of the bending mechanism 215, and/or a desired degree of curvature or contour to which the rod 60 is to be bent, just to name a few possibilities. The user input 240 may include push buttons or touch screen on the handle of the instrument, a keyboard, mouse or other pointing device, a voice recognition input subsystem, and/or different operator input apparatus as would occur to those skilled in the art.

As one example of a response to the indication provided by the display 235, the user can provide an input signal at the user input 240 which indicates that the force applied to the rod 60 through bending mechanism 215 needs to be increased, decreased or maintained, for example. The input signal may be transmitted to the controller 225 along the pathway 225d, received and processed by the controller 225, and a corresponding output signal may be provided by the controller 225 to motor 250 via pathway 225a. Motor 250 is operable to move bending mechanism 215 via actuator 255, and motor 250 is linked to actuator 255 through link 250a, and actuator 255 is linked to bending mechanism 215 through link 255a. Links 250a and 255b may be any suitable mechanical, hydraulic, or electronic type connection. The bending mechanism 215 then provides the desired adjustment in angular orientation which is in turn applied to the engage portion of the rod 60. Furthermore, the controller 225 may direct signals to increase, decrease or maintain the heat applied to the rod 60 by heating element 220 in response to user input or without any user input.

As an additional or alternative response to the output signal provided by the display 235, the user may increase, decrease or maintain the amount of pressure applied to the rod 60 by the bending mechanism 215. For example, the system 200 includes an actuating member 255 structured to provide and regulate actuation of the bending mechanism 215 with motor 250. In one form, motor 250 may include a stepper motor configured to control rotation of the components of the bending mechanism 215 about a pivot point with actuator 255. In another form, the motor 250 and actuating member 255 may be provided as a hydraulic arrangement including a hydraulic device configured to provide and regulate actuation of the bending mechanism 215. In one particular aspect of this form, the device may be configured to provide back pressure in response to an amount of force applied by the bending mechanism 215 to rod 60 to limit the amount of force applied by, and/or the rate of actuation of, the bending mechanism 215. In still other embodiments, the motor 250 and actuating member 255 may be provided with other types of mechanical arrangements configured to provide and regulate actuation of the bending mechanism 215.

When the system 200 includes the motor 250 and actuating member 255, the user can provide an input signal at the user input 240 which indicates the desired amount of pressure, force, or degree of bend to be applied to the rod 60 by the bending mechanism 215. The input signal may be transmitted to the controller 225 along the pathway 225d, received and processed by the controller 225, and a corresponding output signal may be provided by the controller 225 to the motor 250 via pathway 225a. The actuating member 255 is linked between motor 250 and bending mechanism 215. While the motor 250, actuating member 255 and the bending mechanism 215 have been illustrated as separate components, it should be appreciated that in alternative embodiments, these separate components could be combined into a single component. Furthermore, as alternatives to the foregoing, the controller 225 may automatically regulate the pressure applied on the rod 60 by the bending mechanism 215 in response to the sensor signal without any user input, or a user could directly input a pressure change at the motor 250 or actuating member 255 in response to the indication provided by the display 235.

In one embodiment, system 200 is configured to provide real-time, dynamic control of an in situ rod bending process while minimizing or eliminating the manual forces to be applied to the rod during bending. For example, system 200 may be configured to automatically control the amount of force, pressure and/or heat applied to the rod 60 during the bending process to avoid undesired deformation of the rod 60 or a negative effect on the material properties of the rod 60. In one particular form of control, the system 200 is configured to gradually increase the bend in the rod 60 until a desired curvature or contouring of the rod 60 is achieved. Once the desired configuration is achieved, the system 200 can then be removed from the rod 60. Since bending of rod 60 takes place in situ, the rod 60 should provide an optimal fit with the implanted construct. However, system 200 can be readily re-engaged in situ to rod 60 to apply more or additional bends to rod 60 as desired.

Figure 17:
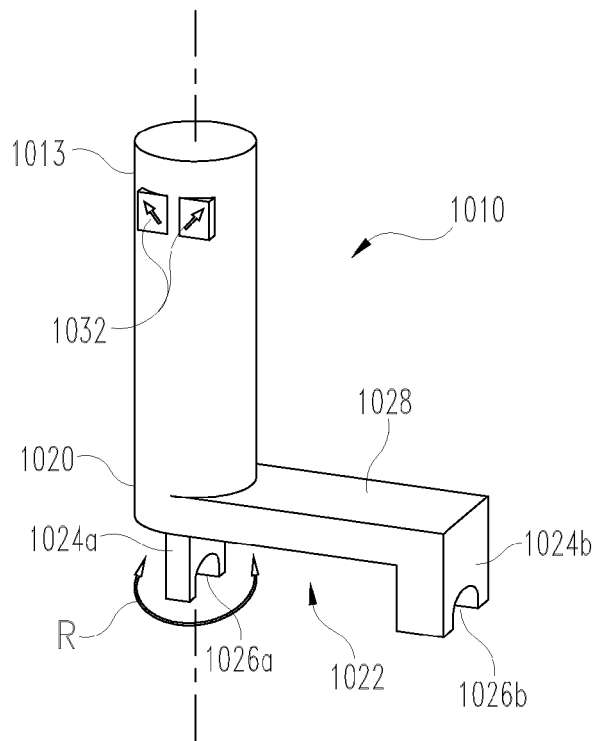
FIG. 17 is a perspective view of another embodiment bending instrument.

In another embodiment, FIG. 17 shows a distal portion of a bending instrument 1010, and the proximal portion 1013 of the bending instrument 1010 can be configured identically to the other bending instruments described herein. The distal portion in FIG. 17 includes another embodiment bending mechanism 1022 that includes a first implant engaging member 1024a extending distally from and rotatably coupled to distal shaft portion 1020 on longitudinal axis L. A second implant engaging member 1024b is offset laterally from first implant engaging member 1024a. Second implant engaging member 1024b includes a coupling portion 1026b that is non-pivotally mounted to a rigid arm 1028 that extends laterally from distal shaft portion 1020. First implant engaging member 1024a is articulated by rotating it around longitudinal axis L, resulting in articulation of first implant engaging member 1024a around a rotation path R to change the angular orientation channel 1026a of first implant engaging member 1024a relative to longitudinal axis L and relative to second implant engaging member 1024b. Thus, an elongate member extending through the channels of implant engaging members 1024a, 1024b is bent in a direction that is normal to the direction in which the previous bending instrument embodiments bend the elongate member. In one particular application for a spinal rod positioned between anchors engaged to pedicles of vertebrae, the previous bending instrument embodiment provide bending or contouring of the rod primarily in or parallel to the sagittal plane, while the bending instrument of FIG. 17 provides bending or contouring of the rod primarily in or parallel to the coronal plane.

Instrument 1010 includes a set of controls 1032 operable to receive input and provide signals to the actuator to the actuator to adjust the rotational orientation of implant engaging member 1024a relative to longitudinal axis L by rotating implant engaging member 1024a along path R and relative to the implant engaging member 1024b. The elongate spinal implant engaged to implant engaging members 1024a, 1024b is thus bent with implant engaging member 1024b holding the elongate implant in position while implant engaging member 1024a rotates to bend the elongate spinal implant.

Figure 18:
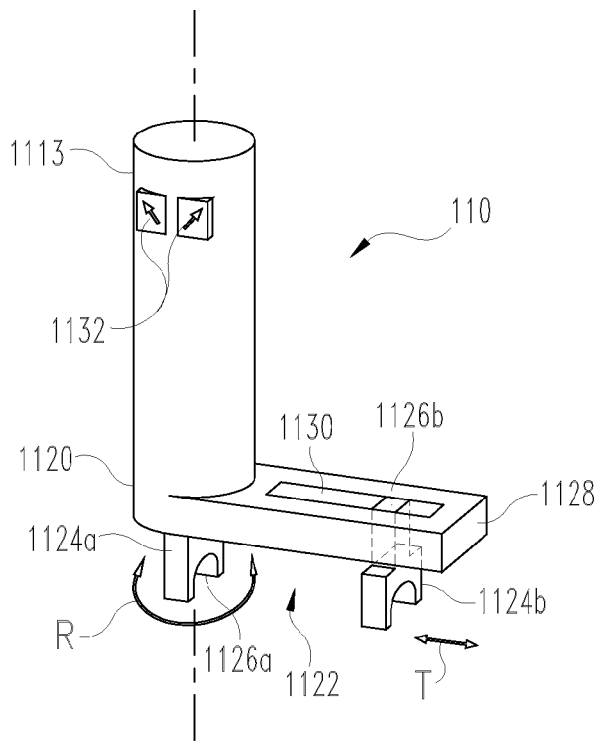
FIG. 18 is a perspective view of another embodiment bending instrument.

In a further variation of the embodiment of FIG. 17, FIG. 18 shows a bending instrument 1110, and the proximal portion 1113 of the bending instrument 1110 can be configured identically to the other bending instruments described herein. The distal portion in FIG. 18 includes another embodiment bending mechanism 1122 that includes a first implant engaging member 1124a that is similar to implant engaging member 1024a discussed above. A second implant engaging member 1124b is offset laterally from first implant engaging member 1124a. Second implant engaging member 1124b includes a coupling portion 1126b that is received in a slot 1130 of a rigid arm 1128 that extends laterally from distal shaft portion 1120. First implant engaging member 1124a is articulate by rotating it relative to distal shaft portion 1120 about longitudinal axis L on path R, and second implant engaging member 1124b can translate laterally in slot 1130 along translation path T to adjust the lateral spacing between implant engaging members 1124a and 1124b.

In one embodiment, a bending instrument for bending an elongate surgical implant is provided. The bending instrument includes a bending mechanism with an implant engaging member. The bending mechanism is movably coupled to a proximal portion of the bending instrument. The bending mechanism is operable to change angular orientations of the implant engaging member relative to the proximal portion of the bending instrument to bend the elongate implant while the implant is engaged by a second implant engaging member that holds the implant in position.

In still another embodiment, a system includes a pair of laterally spaced bending instruments or instrument portions that each includes bending mechanism with an engaging member for engaging an elongate implant in situ. At least one of the bending mechanisms movably couples the implant engaging member to a proximal portion of the respective bending instrument or instrument portion. The bending mechanism is operable to change the orientation of the implant engaging member relative to the proximal portion to apply bending forces to the elongate implant when the elongate implant is positioned in the implant engaging members. In one embodiment, the elongate implant is the only structure that links the bending instruments to one another, enhancing placement of the bending instruments relative to one another and relative to the elongate implant to apply the bending forces at the optimal locations along the elongate implant. In another embodiment, a linking member extends between and couples the implant engaging members to one another.

In yet another embodiment, a method for bending an elongate implant of an orthopedic construct includes providing at least one bending instrument including a bending mechanism that couples an implant engaging member of the bending instrument with a proximal portion of the bending instrument. The proximal portion includes a handle of the bending instrument, and the bending mechanism is operable to change the orientation of the implant engaging member relative to the proximal portion so that when the elongate implant is implanted in the patient the elongate member can be bent by articulating the implant engaging member relative to the proximal portion of the instrument and relative to the other implant engaging member while holding the elongate implant with the other implant engaging member associated with the first implant engaging member.

Any theory, mechanism of operation, proof, or finding stated herein is meant to further enhance understanding of the present invention, and is not intended to make the present invention in any way dependent upon such theory, mechanism of operation, proof or finding. It should be understood that while the use of the word preferable, preferably or preferred in the description above indicates that the feature so described may be more desirable, it nonetheless may not be necessary, and embodiments lacking the same may be contemplated as within the scope of the application, that scope being defined by the claims that follow. In reading the claims, it is intended that when words such as "a", "an", "at least one", and "at least a portion" are used, there is no intention to limit the claim to only one item unless specifically stated to the contrary in the claim. Further, when the language "at least a portion" and/or "a portion" is used, the item may include a portion and/or the entire item unless specifically stated to the contrary.

While the application has been illustrated and described in detail in the drawings and foregoing description, the same is to be considered as illustrative and not restrictive in character, it being understood that only the selected embodiments have been shown and described and that all changes, modifications and equivalents that come within the spirit of the invention as defined herein or by any of the following claims are desired to be protected.

What is claimed is:

1. A system for bending a surgical construct, comprising:
an elongate spinal implant;
a proximal handle portion extending along a longitudinal axis from a proximal end to a distal shaft portion opposite said proximal end; and
a bending mechanism including at least one first implant engaging member pivotally coupled to said distal shaft portion and a second implant engaging member, said first and second implant engaging members each including a channel extending therethrough for receiving said elongate spinal implant in a transverse orientation to said longitudinal axis, said bending mechanism including a first drive member coupled to said distal shaft portion and a second drive member coupled to said first implant engaging member, wherein said bending mechanism is operable to articulate said first implant engaging member relative to said distal shaft portion and said second implant engaging member to change an angular orientation of said first implant engaging member relative to said longitudinal axis to bend said elongate spinal implant when positioned in said channels of said first and second implant engaging members, further comprising a heating element in said first implant engaging member, said heating element extending along said channel and being arranged to apply heat to a portion of said elongate spinal implant when said elongate spinal implant is positioned within said channel of first said implant engaging member.

2. The system of claim 1, wherein
said first drive member is rotatable coupled adjacent said distal shaft portion;
said second drive member is fixedly coupled to said first implant engaging member in engagement with said first drive member;
further comprising an actuator coupled to said first drive member, wherein movement of said actuator rotates said first drive member relative to said distal mounting portion, and rotation of said first drive member rotates said second drive member to pivot said implant engaging member relative to said longitudinal axis; and
said first drive member includes a first pulley and said second drive member includes a second pulley, and further comprising a roller mounted to said distal shaft portion between said first pulley and said second pulley and a drive belt positioned against said roller, wherein said driver belt is engaged to each of said first and second pulleys.

3. The system of claim 1, wherein said distal shaft portion includes a rigid arm extending laterally therefrom and said second implant engaging member is rigidly fixed to said rigid arm.

4. A system for bending a surgical construct, comprising:
an elongate spinal implant;
a proximal handle portion extending along a longitudinal axis from a proximal end to a distal shaft portion opposite said proximal end; and
a bending mechanism including at least one first implant engaging member pivotally coupled to said distal shaft portion and a second implant engaging member, said first and second implant engaging members each including a channel extending therethrough for receiving said elongate spinal implant in a transverse orientation to said longitudinal axis, said bending mechanism including a first drive member coupled to said distal shaft portion and a second drive member coupled to said first implant engaging member, wherein said bending mechanism is operable to articulate said first implant engaging member relative to said distal shaft portion and said second implant engaging member to change an angular orientation of said first implant engaging member relative to said longitudinal axis to bend said elongate spinal implant when positioned in said channels of said first and second implant engaging members, wherein said distal shaft portion includes a rigid arm extending laterally therefrom and said first implant engaging member is pivotally coupled to said rigid arm and said second implant engaging member extends from said distal shaft portion in fixed relation to said distal shaft portion.

5. The system of claim 4, wherein said proximal handle portion includes a gripping portion adjacent said proximal end, said gripping portion including a pressure sensing pad configured to sense a pressure applied to said gripping portion.

6. The system of claim 4, further comprising a passage extending from a port that opens into said channel of said at least one of said first and second implant engaging members, said port being positioned to allow material to pass from said passage to said elongate spinal implant when said elongate spinal implant is positioned within said channel.

7. The system of claim 4, wherein said first implant engaging member is translatable along said rigid arm toward and away from said second implant engaging member.

8. A system, comprising:
a first bending instrument and a second bending instrument laterally spaced from said first bending instrument, each of said first and second bending instruments including:
an elongate handle portion extending along a longitudinal axis and a distal shaft portion extending distally from said elongate handle portion along said longitudinal axis and an implant engaging member extending distally from said distal shaft portion, said implant engaging members defining a channel;
at least one of said first and second bending instruments including a bending mechanism including said implant engaging member pivotally coupled to said distal shaft portion thereof, a first drive member coupled to said distal shaft portion, and a second drive member coupled to said implant engaging member and connected with said first drive member, wherein at least one of said first and second drive members is movable to rotate said implant engaging member about said pivotal coupling location to change an angle of orientation of said implant engaging member relative to said longitudinal axis;
an elongate spinal implant extending through said channels of said implant engaging members when said implant engaging members are in a first angular orientation relative to said longitudinal axis; and
wherein rotation of said at least one of said first and second drive members of said at least one of said first and second bending instruments moves said implant engaging member from said first angular orientation to a second angular orientation while the other of said first and second bending instruments maintains said elongate spinal implant in position, wherein said spinal implant is bent as said implant engaging member moves from said first angular orientation to said second angular orientation.

9. The system of claim 8, wherein said implant engaging member of said at least one of said first and second bending instruments is aligned with said longitudinal axis in said first angular orientation, and said implant engaging member of said at least one of said first and second bending instruments moves along a pivot path to said second angular orientation, said second angular orientation forming an angle ranging from more than 0 degrees to at least 90 degrees relative to said longitudinal axis.

10. The system of claim 8, further comprising:
at least one sensor structured and arranged to monitor one or more operating functions of said at least one of said first and second bending instruments and to provide a corresponding sensor output signal;
a controller responsive to the sensor output signal to determine if changes in said one or more operating functions are desired;
a motor connected to said controller and to said bending mechanism, said motor being operable in response to signals from said controller to move said at least one of said first and second drive members.

11. The system of claim 8, further comprising a rigid arm extending between and rigidly coupling said first and second bending instruments to one another.

12. A method for bending an elongate spinal implant associated with an orthopedic construct implant within a patient, comprising:
providing an elongate spinal implant;
providing an instrument including a proximal handle portion and a bending mechanism structured to receive a portion of the elongate spinal implant, the instrument further including an actuation system connected to the handle portion and the bending mechanism;
positioning a portion of the elongate spinal implant within first and second engaging members of the bending mechanism when the elongate spinal implant is in the patient; and
bending the elongate spinal implant by actuating the bending mechanism to articulate at least one of the first and second implant engaging members relative to the other of the first and second implant engaging members while holding the elongate spinal implant in position with the other of the first and second implant engaging members.

13. The method of claim 12, further comprising increasing the temperature of the elongate spinal implant to increase a flexibility of the elongate spinal implant prior to bending the elongate spinal implant, wherein the at least one of the first and second implant engaging members includes an implant engaging member with a channel for receiving the elongate spinal implant and a heating element in the channel in contact with the elongate spinal implant.

14. The method of claim 12, further comprising monitoring a pressure applied to the elongate spinal implant during the bending and controlling an amount of pressure applied to the elongate spinal implant in response to the monitoring.

* * * * *